United States Patent [19]

Kim et al.

[11] Patent Number: 4,889,723
[45] Date of Patent: Dec. 26, 1989

[54] PHARMACEUTICAL COMPOSITIONS COMPRISING ESTERS OR AMIDES AS ACTIVE INGREDIENTS

[75] Inventors: Soonih Kim; Kazuhisa Takeda; Seiei Sasatani, all of Osaka, Japan

[73] Assignee: Ono Pharmaceutical Co., Ltd., Osaka, Japan

[21] Appl. No.: 180,933

[22] Filed: Apr. 13, 1988

[30] Foreign Application Priority Data

Apr. 13, 1987 [JP] Japan .................................. 62-88785

[51] Int. Cl.$^4$ ............................................. H61K 37/22
[52] U.S. Cl. .................................... 424/450; 424/451; 424/456; 424/463
[58] Field of Search ................ 424/463, 495; 514/539, 514/562

[56] References Cited

U.S. PATENT DOCUMENTS

| | | | |
|---|---|---|---|
| 4,305,936 | 12/1981 | Klein | 514/174 |
| 4,443,477 | 4/1984 | Witte et al. | 514/539 |
| 4,486,471 | 12/1984 | Samejima et al. | 424/495 |
| 4,716,178 | 12/1987 | Scherrer et al. | 514/562 |

*Primary Examiner*—Thurman Page
*Assistant Examiner*—P. L. Prater
*Attorney, Agent, or Firm*—Sughrue, Mion, Zinn, Macpeak and Seas

[57] ABSTRACT

The present invention relates to new pharmaceutical compositions characterizing that esters or amides are suspended or dissolved in a middle chain glyceride or a mixure thereof. These pharmaceutical compositions inhibit the degradation of the active ingredient (i.e. esters or amides) by the action of various digestive enzymes in digestive system.

9 Claims, 5 Drawing Sheets

PHARMACEUTICAL COMPOSITIONS COMPRISING ESTERS OR AMIDES AS ACTIVE INGREDIENTS

FIELD OF THE INVENTION

The present invention is concerned with new pharmaceutical compositions comprising esters or amides as active ingredients. More particularly, it relates to pharmaceutical compositions characterizing that esters or amides are suspended or dissolved in middle chain glycerides (referred to as "MCG" hereafter) or mixtures thereof. The degradation of the esters or amides by digestive enzymes (e.g. esterases and peptidases) is inhibited by suspending or dissolving the said esters or amides in MCGs.

BACKGROUND OF THE INVENTION

Out of many esters, various esters of guanidinobenzoic acid are known to be useful as medicines, for example, useful in the treatment of acute pancreatitis etc. owing to their anti-plasmin activity and anti-trypsin acitivity and in the treatment of pulmonary emphysema etc. owing to their inhibitory activity on elastase.

Recently, As a result of their detailed research on pharmacokinetics in oral administration of the above esters, the present inventors have found unexpected facts. That is, it has been confirmed that these esters are degraded by the action of various esterase in digestive system, especially in intestine comparatively rapidly.

Esters of guanidinobenzoic acid are degraded to guanidino benzoic acid and an alcohol corresponding to the ester moiety (when a medicine has plural esterbonds, it is presumed that the bonds is severed in order of facility in breaking and finally the medicine is degraded to guanidinobenzoic acid and another part. Any degradation products have no desired pharmacological effect or have the structure not to be absorbed, and therefore, the bioavailability of the esters of guanidinobenzoic acid descends.

Furthermore, it has turned out that other esters and amides which are considered to be degraded by the action of various esterases and peptidases in digestive system, are degraded comparatively rapidly, similarly to esters of guanidinobenzoic acid.

As a result of their energetic investigation in order to find means to inhibit the degradation of the esters or amides by the action of digestive enzymes (e.g. various esterases and peptidases) in digestive system, the present inventors have find that the purpose is accomplished by suspending or dissolving the said esters or amides in MCGs, and having completed the present invention.

In the specification of the Japanese Patent Kokai No. 55-17328, W/O/W-formed emulsion comprising insulin as active agent and middle chain triglycerides (referred to as "MCT" hereafter) etc. as oily substance, and inhibiting the degradation by the action of digestive enzymes, is disclosed. In the composition, MCT is used as oily substance which the oily phase in W/O/W-formed emulsion is composed of. At the point, there is fundamental difference in structure from the MCG suspensions or solutions of the present invention, and further, such W/O/W-formed emulsion does not suggest the present invention at all.

Furthermore, no other prior arts relating to MCGs suspensions or solutions for inhibiting the degradation of active ingredients by the action of digestive enzymes, have been known. Further, no compositions comprising suspensions or solutions of guanidinobenzoic acid derivatives in MCGs have so far been known.

CONSTITUTION OF THE INVENTION

Accordingly, the present invention is concerned with pharmaceutical compositions characterizing that esters or amides (except for glycosides, cyclospolins, antibiotics and nifedipine) are suspended or dissolved in middle chain glycerides (referred to as "MCG" hereafter) or a mixture of two or more of them.

As esters used in the present invention, any compounds having ester bonds (—COO—) in their chemical structure are included. However, the compositions comprising glycosides, antibiotics having ester bonds and nifedipine, with MCGs are already disclosed in the specifications of the British Patent Publication No. 1544576, the European Patent Publication No. 108295 and the Japanese Patent Kokai Nos 58-170788 and 59-106418, and therefore, are excluded from the present invention.

As the esters used, esters of benzoic acid and esters of thromboxane analogues are preferred.

In the esters of benzoic acid, compounds being an ester of p-guanidinobenzoic acid as fundamental chemical structure are preferred. Especially preferably, the esters are compounds of the general formula:

(I)

(wherein R is an organic group) and non-toxic acid-addition salts thereof. They are described in detail, for example, in the specification of the Japanese Patent Kokai Nos. 50-4038, 51-16631, 51-54530, 51-75042, 52-89640, 53-147044, 54-70241, 55-55154, 55-100356, 55-115863, 55-115865, 56-34662 and 57-53454, and of the British Patent Nos. 1472700, 2007653, 2044760 and 2057435, and of the European Patent Publication No. 222608. Compounds wherein R is a substituted armatic groups in the general formula (I) are more preferred. Such compound are p-(p-guanidinobenzoyloxy)-phenylacetic acid N,N-dimethylcarbamoylmethyl ester, p-guanidinobenzoic acid p-sulfamoylphenyl ester, p-guanidinobenzoic acid 6-amidinonaphth-2-yl ester etc. and non-toxic acid-addition salts thereof. p-guanidinobenzoic acid methyl ester and non-toxic acid-addition salts thereof are also preferred.

Other preferable esters of benzoic acid are esters of salicylic acid. Such compounds are aspirin and salicylic acid ethyl ester.

The esters of thromboxane analogues are another preferred esters used in the present invention. More preferably, the esters are the compounds described in the specification of the British Patent Publication No. 2184118 and of the European Patent Publication Nos. 44771 and 171146. Such compounds are, for example, alkyl esters of 7-(3-tosylaminobicyclo[2.2.1]heptan-2-yl)-5Z-heptenoic acid.

As amides used in the present invention, any compounds having amido bonds (—CONH—) in their chemical structure are included. However, the compositions comprising cyclosporins and antibiotics having amido bonds, with MCGs are already disclosed in the specification of the British Patent Publication No. 2015339 and of the European Patent Publication No. 108295 and of the Japanese Patent Kokai No. 58-170788, and therefore, are excluded from the present invention.

As the amides used, amides of prostaglandin analogues, amides of benzoic acid, amides of thromboxane analogues and prolinal or thiazolidine derivatives having amido bonds.

In the amides of prostaglandin analogues, the preferred compounds are disclosed in the specifications of the European Patent Publication Nos. 156611, 182231 and 232126, and of the French Patent Publication No. 2376134 and further in the Chemical Abstracts, abstract Nos. 77743g (1976), 43438a (1976) and 131213h (1975). Such compounds are, for example, amides of 6-keto-16S, 18S-ethano-20-ethyl-$PGE_1$ with an amino acid.

In the amides of benzoic acid, the preferred compounds are disclosed in the specification of the European Patent Publication No. 173516.

In the amides of thromboxane analogues, the preferred compounds are disclosed in the specification of the Japanese Patent Application No. 62-266501. Such compounds are, for example, amides of 7-(3-tosylaminobicyclo[2.2.1]heptan-2-yl)-5Z-heptenoic acid with an amino acid.

In the prolinal or thiazolidine derivatives having amido bonds, the preferred compounds are disclosed in the specification of the European Patent Application No. 87116613.8 and of the Japanese Patent Application No. 62-37844. Such compounds are, for example, N-[3-[N-(4-chlorobenzyl)carbamoyl]propanoyl]-L-prolinal.

Pharmacological effects of esters or amides used in the compositions of the present invention are not limited. For example, the esters of p-guanidinobenzoic acid of the general formula (I) have inhibitory effects on proteinases such as anti-plasmin activity, anti-trypsin activity etc., and therefore may be useful in the treatment of acute pancreatitis etc., or they have an inhibitory effect on elastase, and therefore may be useful in the treatment of pulmonary emphysema.

MCGs in the present invention mean a monoglyceride of a fatty acid of 4 to 10 carbon atoms (referred to as "MCM" hereafter), a corresponding diglyceride (referred to as "MCD" hereafter) and a corresponding triglyceride (referred to as "MCT" hereafter), and a mixture of two or more of them. The fatty acids having any carbon atoms are preferred. Glycerides of caprylic acid and of capric acid are more preferred. Glyceryl monocaprylate, glyceryl dicaprylate and glyceryl tricaprylate, and a mixture thereof are especially preferred. MCGs used in the present invention are on the market with trade marks, e.g. Migryol and Imwitor (both prepared by Dynamite Novel Co.) and Panacete (prepared by Nippon Yushi Co.).

The suspension composition or solution composition of the present invention may, if desired, comprise other inert additional substances, for example, viscosity-lowing agents such as phospholipids and non-ionic surface-active agents, and specific gravity-controlling agents such as calcium carbonate, calcium citrate and calcium gluconate.

The pharmaceutical compositions of the present invention may be prepared by adding esters or amides, and, if desired, other additional substances into MCGs, and suspending or dissolving the mixture by known methods.

The obtained suspensions or solutions may be administrated as it is (directly), and preferably administered in the form of capsules formulations filled into gelatin-made soft capsules or gelatin-made hard capsules. If necessary, the said capsules formulation may be coated with enteric coating. Any enteric coatings being unreactive with active ingredients may be used. Preferable examples of enteric coatings used are carboxymethylethyl cellulose, hydroxypropylmethyl cellulose acetate succinate and phospholipids. The preparation of capsules and the coating with enteric coating may be carried out by known methods.

EFFECTS

The pharmaceutical compositions of the present invention may inhibit the degradation of esters or amides by the action of digestive enzymes in digestive system, and therefore the bioavailability of the active ingredient remarkably ascends.

EXAMPLES

The following examples, reference examples and experiments illustrate, but not limit, the present invention in detail.

Example 1

A mixture of 250 g of p-(p-guanidinobenzoyloxy)-phenylacetic acid N,N-dimethylcarbamoylmethyl ester methanesulfonate, 740 g of glyceryl tricaprylate (Panacete® 800, prepared by Nippon Yushi Co.) and 10 g of bean lecithin (prepared by Hohnen Seiyu Co.) was stirred enough and then sieved through a 100-mesh sieve to obtain the desired suspension of the present invention.

Example 2

By the same procedure as described in Example 1, the suspension of the present invention was obtained by using 250 g of p-guanidinobenzoic acid 6-amidinonaphth-2-yl ester dimethanesulfonate, 740 g of glyceryl tricaprylate and 10 g of bean lecithin.

Example 3

By the same procedure as described in Example 1, the suspension of the present invention was obtained by using 50 g of p-guanidinobenzoic acid p-sulfamoylphenyl ester methanesulfonate, 940 g of glyceryl monocaprate (Panacete® 1000, prepared by Nippon Yushi Co.) and 10 g of bean lecithin.

Example 4

By the same procedure as described in Example 1, the suspension of the present invention was obtained by using 50 g of p-guanidinobenzoic acid methyl ester methanesulfonate, 940 g of glyceryl monocaprylate (Imwitor® 742, prepared by Dynamite Novel Co.) and 10 g of bean lecithin.

Example 5

By the same procedure as described in Example 1, the suspension of the present invention was obtained by using 250 g of p-(p-guanidinobenzoyloxy)phenylacetic acid N,N-dimethylcarbamoylmethyl ester methanesulfonate, 740 g of a mixture of glyceryl monocaprylate and glyceryl dicaprylate (6:4) (Imwitor® 908, prepared by Dynamite Novel Co.) and 10 g of bean lecithin.

Example 6

980 g of glyceryl tricaprylate were added little by little to 20 g of 7-[(1R, 2S, 3S, 4S)-3-tosylaminobicyclo[2.2.1]heptan-2-yl]-5Z-heptenoic acid ethyl ester and the mixture was stirred enough to obtain the desired solution of the present invention.

Example 7

By the same prosedure as described in Example 1, the soution of the present invention was obtained by using 250 g of aspirin, 740 g of a mixture of glyceryl monocaprylate and glyceryl dicaprylate (6:4) and 10 g of bean lecithin.

Example 8

50 ml of ethanol was added to 250 g of salicylic acid ethyl ester with stirring to give semi-solid solution. To the mixture was added 750 g of glyceryl tricaprylate and the obtained mixture was stirred enough. Ethanol was removed completely from the mixture under vacuum more than an overnight to obtain the suspension of the present invention.

Example 9

10 ml of ethanol was added to 20 g of an amide of 6-keto-16S,18S-ethano-20-ethyl-PGE$_1$ with L-leucine. To the obtained solution was added 980 g of glyceryl tricaprylate and the mixture was stirred enough. Ethanol was removed completely from the mixture under vacuum more than an overnight to obtain the solution of the present invention.

Example 10

A mixture of 50 g of an amide of 7-[(1R, 2S, 3S, 4S)-3-tosylaminobicyclo[2.2.1]heptan-2-yl]-5Z-heptenoic acid with glycine, 940 g of glyceryl monocaprylate and 10 g of polyoxyethylenehydrogenated caster oil (HCO-60®, prepared by Nikko chemicals Co.) was stirred enough to obtain the suspension of the present invention.

Example 11

By the same procedure as described in Example 1, the suspensionn of the present invention was obtained by using 250 g of N-[3-[N-(4-chlorobenzyl)carbamoyl]-propanoyl]-L-prolinal, 740 g of glyceryl tricaprylate and 10 g of bean lecithin.

Reference Example 1

1000 g of the suspension prepared in Example 1 were filled into water-soluble soft capsules with a rotary-capsule machine by methods known per se to obtain about 2500 capsules.

Reference Example 2

The soft capsules prepared in Reference Example 1 were coated with an aqueous solution containing 12% (w/v) carboxymethylethyl cellulose (CMEC.AQ®, prepared by Freund Sangyo Co.), 3% (w/v) glyceryl caprylate and 1% (w/v) sodium citrate by pan-coating method to obtain enteric-coated soft capsules.

Reference Example 3

The soft capsules prepared in Reference Example 1 were coated with an aqueous solution containing 10% (w/v) hydroxypropylmethyl cellulose acetate succinate (HPMCAS ®, prepared by Shin-etsu Kagaku Co.), 2% (w/v) triethyl citrate, 5% (w/v) talc and 0.05% (w/v) hydroxypropylcellulose (HPC-MF®, prepared by Shin-etsu Kagaku Co.) by pan-coating method to obtain enteric-coated soft capsules.

Reference Example 4

1000 g of each suspension or solution prepared in Example 2 to 11 were filled into water-soluble soft capsules with a rotary-capsule machine by methods known per se to obtain 2500 each capsules (100 mg of the active ingredient were contained in each capsules obtained from the composition of Example 2, 5, 7, 8 and 11, and 20 mg of the active ingredient were contained in each capsules obtained from the composition of Example 3, 4 and 10, and further 8 mg of the active ingredient were contained in each capsules obtained from the composition of Example 6 and 9).

Reference Example 5

By the same procedure as described in Reference Example 2, enteric-coated soft capsules were obtained by using soft capsules prepared in Reference Example 4.

Reference Example 6

By the same procedures as described in Reference Example 3, enteric-coated soft capsules were obtained by using soft capsules prepared in Reference Example 4.

Reference Example 7

1000 g of the suspension or solution prepared in Example 1 to 11 were filled into water-soluble hard capsules with an oil and paste filling machine by methods known per se to obtain about 2500 each capsules.

Reference Example 8

By the same procedures as described in Reference Example 2 or 3, enteric-coated hard capsules were obtained by using hard capsules prepared in Reference Example 7.

EXPERIMENT 1

The inhibitory effect of MCG on the degradation of esters of quanidinobenzoic acid in small intestine

The experiment was carried out according to the Yasuhara's method using intestinal loop in rats [see Journal of Pharmacobio-Dynamics, 2, 251 (1979)]. That is, male Sprague-Dawley rats weighing 220–260 g were fasted an overnight prior to surgery; however drinking water was readily accessible. The rats were anesthetized by sodium pentobarbital using an intraperitoneal injection of 50 mg/kg. The small intestine was exposed by a midline abdominal incision. The intestinal loop studied was used approximately 15 cm of the duodenal-jejunal site that was approximately 2 cm off the outlet of bile duct.

The suspension or solution containing active ingredients was directly administered into the loop and the both ends of the loop were closed. The experiment with Compound G and I was carried out further by adding pancreatic juice and bile of other rats into the loop by cannula. After a given period of time, the loop was cut out. The contents were washed out with physiological salt solution and/or ethanol, and thereto was added a mixture of 0.1N aqueous methanesulfonic acid, 1,2-dichloroethane and isopropanol. The obtained mixture was centrifuged and the resulting supernatant was used as a sample. In the case of Compound D to H, the washings were directly used as a sample. The active ingredient and the degradation products in sample were determined with high pressure liquid chromatography.

Various esters and amides used in the experiments and administration methods thereof

Compound A: p-(p-guanidinobenzoyloxy)phenylacetic acid N,N—dimethylcarbamoylmethyl ester methanesulfonate

Compound B: p-guanidinobenzoic acid 6-amidinonaphth-2-yl ester dimethanesulfonate

Compound C: p-guanidinobenzoic acid methyl ester methanesulfonate

Compound D: 7-(3-tosylaminobicyclo[2.2.1]heptan-2-yl)-5Z—heptenoic acid ethyl ester

Compound E: salicylic acid ethyl ester

Compound F: aspirin

Compound G: 6-keto-16S,18S—ethano-20—ethyl-PGE$_1$ leucine amide

Compound H: N—[3-[N—(4-chlorobenzyl)carbamoyl]propanoyl]-L-prolinal

Compound I: 7-(3-tosylaminobicyclo[2.2.1]heptan-2-yl)-5Z—heptenoic acid glycine amide (wherein G is a guanidino group.)

Administration method

H₂O: dissolving in the ratio of 5 mg of active ingredient/0.5 ml of water/animal.

MCM8(glyceryl monocaprylate): suspending in the ratio of 5 mg of active ingredient/0.5 ml of MCM8/animal.

MCT8(glyceryl tricaprylate): suspending in the ratio of 5 mg of active ingredient/0.5 ml of MCT8/animal.

Figure 1:
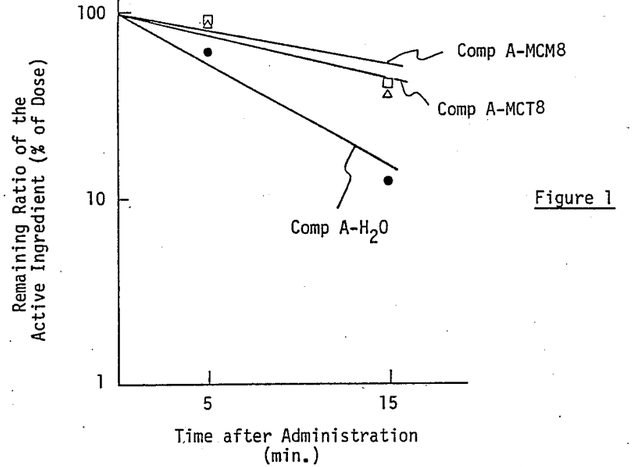
FIGS. 1 to 9 are the time-course of the remaining ratio of the active ingredient in the pharmaceutical composition of the present invention, in small intestine, and FIGS. 1, 2, 3, 4, 5, 6, 7, 8 and 9 relate to Compound A, Compound B, Compound C, Compound D, Compound E, Compound F, Compound G, Compound H and Compound I, respectively.
Figure 2:
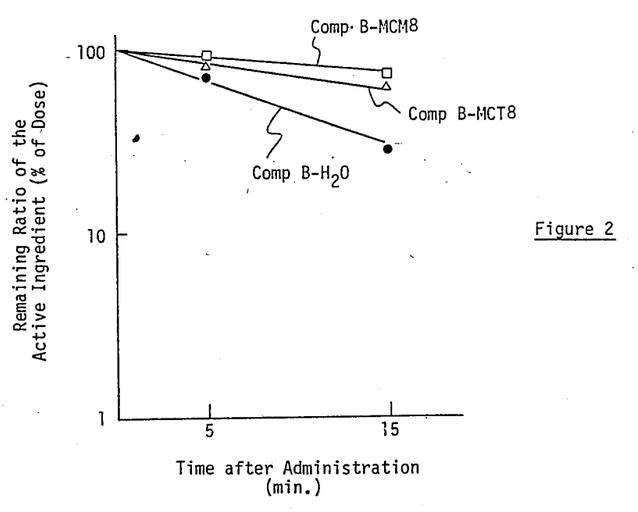
Figure 3:
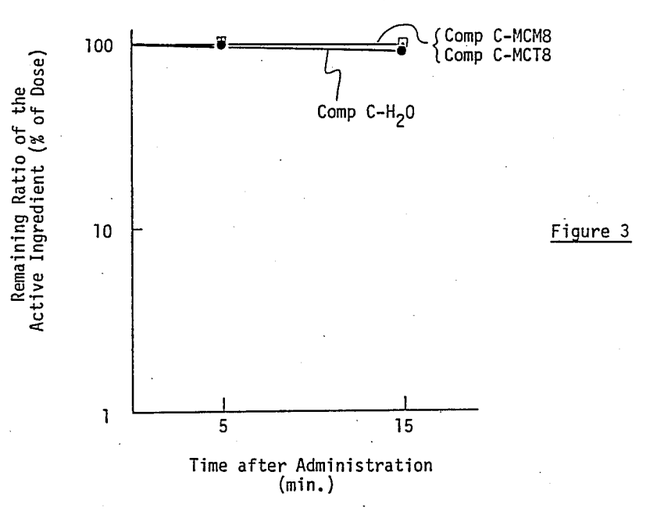
Figure 4:
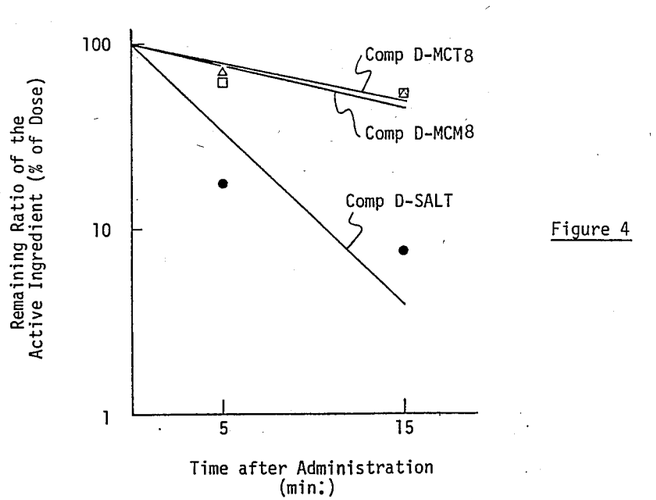
Figure 5:
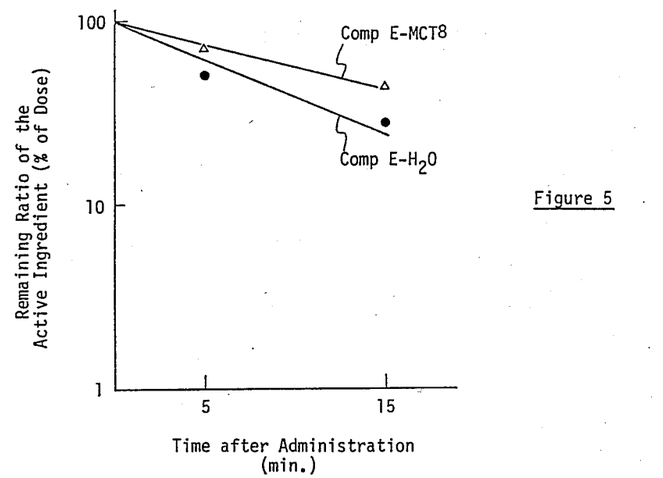
Figure 6:
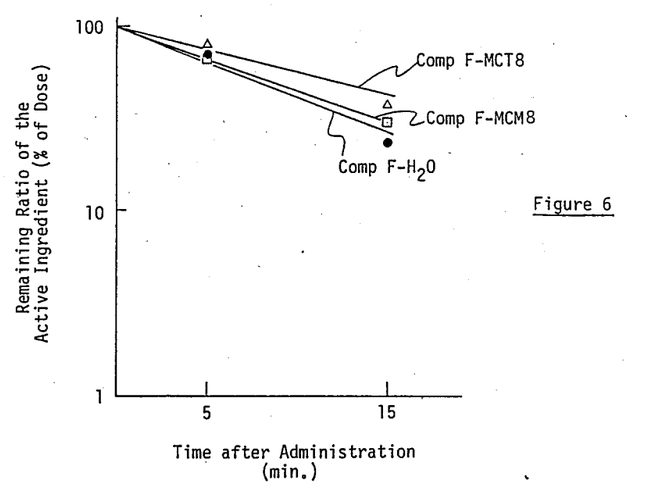
Figure 7:
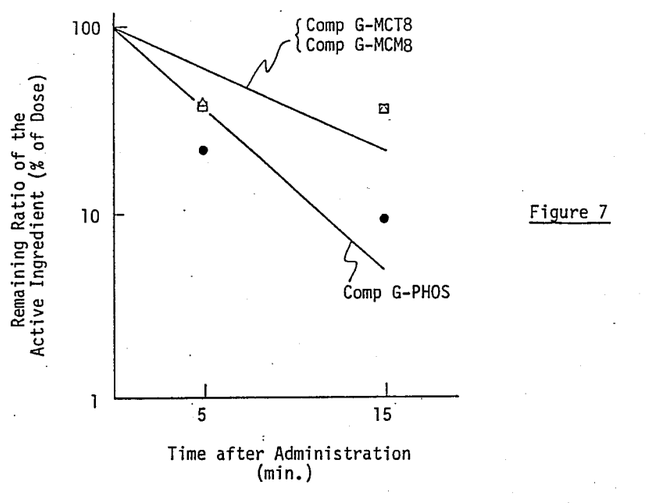
Figure 8:
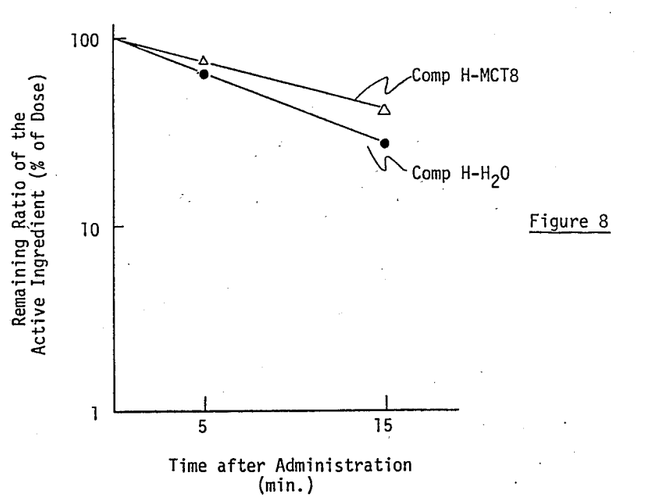
Figure 9:
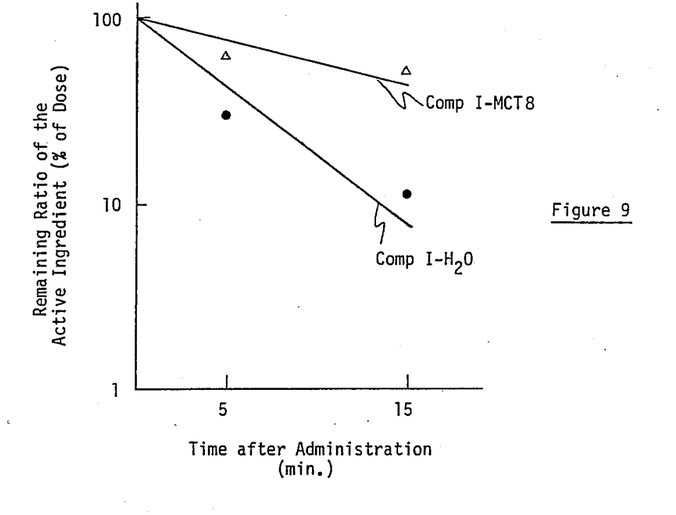

The result was shown in Table 1, and FIGS. 1 to 9.

Notes 1. 0.5 mg of Compound C were used instead of 5 mg of it and the suspension of Compound C even in water was administered because of its poor solubility.

2. 0.5 ml of physiological salt solution (referred to "SALT") for Compound D instead of water, because of its water-insoluble character.

3. 0.1 mg of Compound G were used because of its strong pharmacological effect, and isotonic phosphate buffer solution (referred to "PHOS") (pH 6.5) instead of water was used because of its water-insoluble character.

4. Compound D, E, G, H and I were previously dissolved in 25 μl of ethanol, and then each compositions of H₂O, MCM8 and MCT8, for administration were prepared.

TABLE 1

| Compound | Administration route | Remaining ratio of the active ingredient in small intestine (% of dose, mean ± S.D) | |
|---|---|---|---|
| | | 5 | 15 (minutes after) |
| Compound A | H₂O (COMPARISON) | 58.7 ± 9.6 | 12.7 ± 3.1 |
| | MCM8 (INVENTION) | 85.3 ± 21.8 | 39.7 ± 17.2 |
| | MCT8 (INVENTION) | 82.1 ± 18.5 | 35.5 ± 10.8 |
| Compound B | H₂O (COMPARISON) | 68.8 ± 1.7 | 27.5 ± 5.2 |
| | MCM8 (INVENTION) | 90.0 ± 15.6 | 70.5 ± 12.1 |
| | MCT8 (INVENTION) | 80.0 ± 3.2 | 60.8 ± 7.5 |
| Compound C | H₂O (COMPARISON) | 95.2 ± 3.1 | 85.5 ± 2.5 |
| | MCM8 (INVENTION) | 99.1 ± 3.2 | 95.5 ± 1.5 |
| | MCT8 (INVENTION) | 97.5 ± 2.7 | 92.2 ± 3.4 |
| Compound D | SALT (COMPARISON) | 17.5 ± 2.9 | 7.5 ± 3.4 |
| | MCM8 (INVENTION) | 61.3 ± 9.8 | 52.7 ± 21.0 |
| | MCT8 (INVENTION) | 69.8 ± 12.6 | 52.1 ± 13.1 |
| Compound E | H₂O (COMPARISON) | 49.9 ± 13.7 | 27.3 ± 16.4 |
| | MCT8 (INVENTION) | 70.2 ± 21.0 | 43.5 ± 15.4 |
| Compound F | H₂O (COMPARISON) | 70.5 ± 12.1 | 23.8 ± 15.7 |
| | MCM8 (INVENTION) | 65.9 ± 11.2 | 30.1 ± 5.2 |
| | MCT8 (INVENTION) | 78.7 ± 19.8 | 37.2 ± 11.2 |
| Compound G | PHOS (COMPARISON) | 21.5 ± 8.2 | 9.2 ± 4.4 |
| | MCM8 (INVENTION) | 37.2 ± 5.1 | 35.0 ± 11.3 |
| | MCT8 (INVENTION) | 38.4 ± 12.9 | 35.2 ± 9.8 |
| Compound H | H₂O (COMPARISON) | 62.1 ± 8.3 | 26.3 ± 10.4 |
| | MCT8 (INVENTION) | 74.5 ± 12.4 | 40.0 ± 13.1 |
| Compound I | H₂O (COMPARISON) | 30.4 ± 8.1 | 11.5 ± 8.5 |
| | MCT8 (INVENTION) | 60.8 ± 12.5 | 50.7 ± 11.9 |

From the result of Experiment 1, it is understood that the degradation of active ingredients is inhibited by administrating the suspension or solution of esters or amides in MCG, compared with by administrating the aqueous solution thereof.

EXPERIMENT 2

Effect of MCG on bioavailability (1)

When Experiment 1 was carried out by using Compound A and D, blood was collected after a given period of time (0, 15, 30, 60 and 120 minutes after). The concentration of the active ingredient in blood was determined with high pressure liquid chromatography, and Area Under the plasma concentration-time Curve (AUC) was calculated and then bioavailability (BA) was calculated according to the following formula by comparing with AUC in intravenous administration.

$$BA(\%) = \frac{[AUCid]}{[AUCiv]} \times \frac{[Div]}{[Did]} \times 100$$

[AUCid]: AUC in intraduodenal administration
[AUCiv]: AUC in intravenous administration
[Did]: Dose in intraduodenal administration
[Div]: Dose in intravenous administration

TABLE 2

| | Route | Dose (mg/animal) | AUC (μg · min/ml) | BA (%) |
|---|---|---|---|---|
| Compound A - Saline[1] | iv | 0.5 | 602.9 ± 15.4 | 100 |
| Compound A - H₂O (COMPARISON) | id | 5 | 182.6 ± 55.7 | 3.0 |
| Compound A - MCM8 (INVENTION) | id | 5 | 289.2 ± 72.6 | 4.8 |
| Compound A - MCT8 (INVENTION) | id | 5 | 332.1 ± 169.3 | 5.5 |
| Compound D - Saline[2] | iv | 0.5 | 327.2 ± 79.1 | 100 |
| Compound D - Saline[2] (COMPARISON) | id | 5 | 25.4 ± 17.2 | 0.8 |
| Compound D - MCT8 (INVENTION) | id | 5 | 254.8 ± 102.3 | 7.8 |

[1]Compound A was dissolved in physiological salt solution for intravenous administration.
[2]Ethanol solution of Compound D was diluted with physiological salt solution.

From the result, it is understood that BA in administration of the suspension or solution of esters in MCG is about 1.6 to 9.8 times as superior as BA in administration of aqueous solution of them. The improvement is of great significance.

EXPERIMENT 3

Effect of MCG on bioavailability (2)

Each one soft capsule prepared in Reference Example 1, 2, 3, 4, 5 and 6 (used only a suspension of Example 2 (compound B) in Reference Example 4, 5 and 6) was administered orally with 50 ml of water to six male Beagle dogs fasted an overnight (aged one to two and weighing 10±1 kg). By the same procedures as described in Experiment 2, the concentration of the active ingredient in blood, AUC, and then BA were calculated. The resulte was shown in Table 3.

TABLE 3

|  | Formulation | BA (%) |
| --- | --- | --- |
| Compound A | Reference Example 1 | 10.9 ± 4.3 |
|  | Reference Example 2 | 18.4 ± 7.3 |
|  | Reference Example 3 | 17.2 ± 11.5 |
|  | Comparison A[(1)] | 6.3 ± 2.4 |
| Compound B | Reference Example 4 | 3.2 ± 1.7 |
|  | Reference Example 5 | 5.0 ± 2.5 |
|  | Reference Example 6 | 5.1 ± 2.1 |
|  | Comparison B[(1)] | 1.7 ± 1.2 |

[(1)]Comparison: Compound A or Compound B (10 mg/5 ml of water/kg animal body weight) was orally administered.

From the Table 3, it is understood that BA of the composition in which the active ingredient is suspended in MCG is about 1.5 to 3 times as superior as BA of the composition in which it is not suspended in MCG, even in oral administration.

What is claimed is:

1. A pharmaceutical composition consisting essentially of an ester of a thromboxane analogue or an amide of a thromboxane analogue suspended or dissolved in a middle chain glyceride of a fatty acid of 4 to 10 carbon atoms or mixtures thereof.

2. A pharmaceutical composition according to claim 1, wherein an ester is an ester of benzoic acid.

3. A pharmaceutical composition according to claim 1, wherein an ester of thromboxane analogues is an alkyl ester of 7-(3-tosylaminobicyclo[2.2.1]heptan-2-yl)-5Z-heptenoic acid.

4. A pharmaceutical composition according to claim 1, wherein an amide of thromboxane analogues is an amide of 7-(3-tosylaminobicyclo[2.2.1]heptan-2-yl)-5Z-heptenoic acid with an amino acid.

5. A pharmaceutical composition according to claim 1, wherein the middle chain glyceride is glycerides of caprylic acid or glycerides of capric acid.

6. A pharmaceutical composition accordings to claim 5, wherein the middle chain glyceride is glyceryl monocaprylate, glyceryl dicaprylate or glyceryl tricaprylate, or a mixture thereof.

7. A pharmaceutical composition according to claim 1, which is filled into a capsule.

8. A pharmaceutical composition according to claim 7, characterizing that the capsule is coated with an enteric coating.

9. A pharmaceutical composition according to claim 8, characterizing that the enteric coating is carboxymethylethyl cellulose, hydroxypropylmethyl cellulose acetate succinate or phospholipids.

* * * * *